United States Patent [19]

Konishi et al.

[11] Patent Number: 6,130,081
[45] Date of Patent: Oct. 10, 2000

[54] HIGH-TEMPERATURE DESULFURIZATION BY MICROORGANISMS

[75] Inventors: Jin Konishi; Yoshitaka Ishii; Kouichi Okumura; Masanori Suzuki, all of Shizuoka, Japan

[73] Assignee: Petroleum Energy Center, Tokyo, Japan

[21] Appl. No.: 09/289,296

[22] Filed: Apr. 9, 1999

Related U.S. Application Data

[62] Division of application No. 09/905,778, Jul. 29, 1997, Pat. No. 5,925,560.

[30] Foreign Application Priority Data

Jul. 30, 1996 [JP] Japan ................................ 8-200696

[51] Int. Cl.$^7$ ................ C12P 1/04; C12N 1/20
[52] U.S. Cl. .................. 435/252.1; 435/170; 435/262; 435/282; 435/822
[58] Field of Search ............................. 435/252.1, 170, 435/822, 262, 282

[56] References Cited

U.S. PATENT DOCUMENTS 5,916,781  6/1999  Yamamoto et al. .................. 435/170

OTHER PUBLICATIONS

Computer Derwent Abstract Hirasawa et al WO–9951747 Oct. 14, 1999.

Kargi, "Biological oxidation of Thianthrene, Thioxanthene and Dibenzothiophene by the thermophilic organism *Sulfolobus acidocaldarius*" Biotechnology Letters, vol. 9, No. 7, Jul. 1987 (1987–07) pp. 478–482.

*Primary Examiner*—Herbert J. Lilling
*Attorney, Agent, or Firm*—Fish & Richardson

[57] ABSTRACT

The present invention relates to a method of degrading organic sulfur compounds, in which organic sulfur compounds are decomposed by a microorganism belonging to the genus Paenibacillus and having the ability to decompose organic sulfur compounds. Heterocyclic sulfur compounds can be decomposed by specifically cleaving their C—S bonds under high-temperature conditions.

2 Claims, 5 Drawing Sheets

(Formula 1)

Compound (A)
4-methyldibenzothiophene (Formula 2)

Compound (B)
4,6-dimethyldibenzothiophene (Formula 3)

Compound (D)
3,4,6-trimethyldibenzothiophene

HIGH-TEMPERATURE DESULFURIZATION BY MICROORGANISMS

This application is a divisional of Ser. No. 09/905,778 filed on Jul. 29, 1997, now U.S. Pat. No. 5,925,560.

FIELD OF THE INVENTION

The present invention relates to a method of degrading organic sulfur compounds such as benzothiophene, dibenzothiophene etc. by use of microorganisms. The method of present invention can be used particularly for degradation of organic sulfur compounds contained in fossil fuels such as petroleum etc., thus facilitating removal, from fossil fuels, of sulfur which upon combustion of fossil fuels such as petroleum, coal etc., will be diffused into air as a source of environmental pollution.

BACKGROUND OF THE INVENTION
(1) Conventional Hydrodesulfurization Methods

Although methods such as alkali washing, solvent desulfurization etc. are known to desulfurize hydrocarbon fuels such as petroleum, hydrodesulfurization is the mainstream of desulfurization at present. Hydrodesulfurization is a method for reducing the sulfur content in a product by reacting sulfur compounds in a petroleum fraction with hydrogen in the presence of a catalyst so that they are removed as hydrogen sulfide. The catalyst used includes metal catalysts such as cobalt, molybdenum, nickel, tungsten etc. carried on alumina. For a molybdenum catalyst carried on alumina, cobalt or nickel is added as a cocatalyst to improve its catalytic performance. Hydrodesulfurization using such a metal catalyst is undoubtedly a fairly completed process used widely in all over the world at present. From the point of view of a process for producing petroleum products to cope with stricter environmental regulation, however, there are some problems. Hereinafter, such problems are briefly described.

Because the metal catalyst generally has relatively low substrate specificity, it is considered that this catalyst is suitable for degrading various sulfur compounds to lower the sulfur content in fossil fuels as a whole, but can be insufficient in the effect of desulfurizing a specific sulfur compound group. For example, various heterocyclic organic sulfur compounds still remain in light gas oil after desulfurization. One possible reason for such insufficient desulfurization effect of the metal catalyst is the steric hindrance caused by substituent groups around sulfur atoms in the organic sulfur compounds. Among such substituent groups, the influence of methyl substituent groups on the reactivity of the metal catalyst in hydrodesulfurization has been examined using thiophene, benzothiophene, dibenzothiophene etc. According to the results, the desulfurization reactivity of the metal catalyst is decreased generally with an increasing number of substituent groups, and evidently the reactivity is also affected greatly by the position of the substituent group. It has been reported that the reactivity of the metal catalyst in desulfurizing methylated dibenzothiophenes is greatly affected by the steric hindrance caused by the substituent methyl groups (e.g. Houalla, M., Broderick, D. H., Sapre, A. V., Nag, N. K., de Beer, V. H. J., Gates, B. C., Kwart, H. J. Catalt., 61, 523–527 (1980)). In fact, a wide variety of alkylated derivatives of dibenzothiophenes are known to be present in considerable amounts in light gas oil (e.g. Kabe, T., Ishihara, A. and Tajima, H. Ind. Eng. Chem. Res., 31, 1577–1580 (1992)).

It is assumed that higher reaction temperature or pressure than currently used is required to desulfurize the above organic sulfur compounds resistant to the conventional hydrodesulfurization and that a significant amount of hydrogen to be added is also required. Further, improvements in such hydrodesulfurization processes are estimated to need enormous investments in facilities and costs for operation. Such organic sulfur compounds resistant to hydrodesulfurization are contained as a major species of sulfur compounds in e.g. light gas oil. Therefore, the above-described hydrodesulfurization processes should be significantly improved in order to raise the degree of desulfurization of light gas oil.

On one hand, an enzyme reaction carried out by organisms is characterized in that it proceeds under relatively mild conditions and the rate of an enzyme reaction is comparable to the rate of reaction using a chemical catalyst. Furthermore, numerous enzymes are present so as to suitably deal with a wide variety of in vivo reactions, and it is known that these enzymes generally have significantly high substrate specificities. These characteristics are expected to be utilizable in microbial removal of sulfur from sulfur compounds contained in fossil fuels, that is, microbial biodesulfurization (Monticello, D. J., Hydrocarbon Processing 39–45 (1994)).

Conventional Biodesulfurization Methods:

There are a large number of reports on methods of removing sulfur from petroleum by use of microorganisms. Joachim et al. have observed degrees of desulfurization of 60 to 80% in 2 days by continuous treatment of a highly viscous heavy oil fraction with Pseudomonas HECC39 at 30° C. (Bauch, J., Herbert, G., Hieke, W., Eckart, V., Koehler, M., Babenzin, H. D., Chemical Abstracts 82530y vol. 83 (1975)). Yuda has reported that petroleum is converted into a water-soluble compound by allowing petroleum to be in contact with *Pseudomonas haconensis* (Yuda, S., Unexamined Published Japanese Patent Application No. 75,107,002: Chemical Abstracts 46982j vol. 84 (1976)). In addition, Lee et al. have reported desulfurization of crude oil, heavy light gas oil, kerosine and naphtha by a sulfur-oxidizing strain *Thiobacillus thiooxidans* and a sulfur-reducing strain Pseudomonas sp. (Lee, M. J., Hah, Y. C., Lee, K. W. Chemical Abstracts, 145448s, vol. 85 (1976)). They have examined the desulfurization abilities of various sulfur-oxidizing microorganisms and sulfur-reducing microorganisms, and have reported that *Thiobacillus thiooxidans* has the highest ability to oxidize sulfur and *Pseudomonas putrefaciens* and *Desulfovibrio desulfuricans* have the highest ability to reduce sulfur (Lee, M. J., Hah, Y. C., Lee, K. W. Chemical Abstracts, 156414d, vol. 85 (1976)). Isolation of 7 sulfur-reducing Pseudomonas strains has also been reported by the same group. Further, Eckart et al. have reported oxidative desulfurization of Romashkino crude oil and fuel oil by *Pseudomonas desmolyticum* (Eckart, V., Hieke, W., Bauch, J., Gentzsch, H. Chemical Abstracts, 142230q, vol. 94 (1981); Eckart, V., Hieke, W., Bauch, J., Gentzsch, H. Chemical Abstracts, 147259c, vol. 97 (1982)). For these desulfurization reactions made by microorganisms of the genus Pseudomonas, the degradation products have been identified and it is known that every microorganism whose desulfurization reaction mechanism was revealed makes use of the cleavage reaction to C—C bonds in a sulfur compound molecule contained in oil.

(A) C—C Bond-targeted Biodesulfurization

A systematic study on microbial desulfurization was started by Yamada et al. (Yamada, K., Minoda, Y., Kodama, K., Nakatani, S., Akasaki, T., Agric. Biol. Chem.,32, 840–845 (1968)). They have reported that microorganisms of the genus Pseudomonas decompose dibenzothiophene to give a water-soluble product. The Pseudomonas strains used include *Pseudomonas abikonensis* and *Pseudomonas jianii*. Microbial desulfurization by culturing with a mixture of these 2 strains has been examined by Nakatani et al. (Nakatani, S., Sasaki, T., Kodama, K., Minoda, Y. Yamada, K., Agric. Biol. Chem. 32, 1205–1211 (1968)). In their study, a light gas oil solution containing 5% dibenzothiophene is used as a substrate. Kodama et al. have reported that amino acids or other carbon compounds are essential as cosubstrate for oxidation of benzothiophene and growth of the microorganisms. The microorganisms with desulfurization activity had the metabolism by which C—C bonds in a heterocyclic sulfur compound represented by dibenzothiophene are cleaved, the benzene rings are thereby decomposed, and via a subsequent oxidative reaction cascade, sulfates are released. The reaction mechanism of the carbon-skeleton-attack-type pathway, called Kodama pathway, consists of hydroxylation of an aromatic ring (dibenzothiophene→→ 1,2-dihydroxydibenzothiophene), cleavage of the ring, and oxidation thereof into a water-soluble product (1,2-dihydroxydibenzothio phene→ trans-4 [2-(3-hydroxy)thianenaphthenyl]-2-oxo-butenoic acid, 3-hydroxy-2-formylbenzothiophene). Although this type of reaction is known in the genus Pseudomonas, it has been confirmed that the degradation reaction of dibenzothiophene by this kind of microorganism is catalyzed by the same enzyme group as that participating in naphthalene degradation (Eaton, R. W. and Chapman, P. J., J. Bacteriol., 174, 7542–7554, 1992; Denome, S. A., Stanley, D. C., Olson, E. S. and Young, K. D., J. Bacteriol., 175, 6890–6901, 1993). The studies on the microorganisms revealed the microbial ability to remove dibenzothiophene and substituted dibenzothiophene from a pentane-soluble fraction separated from crude oil. From one such strain *Pseudomonas alcaligenes* (DBT-2), 25 kb DNA involved in oxidation of dibenzothiophene was isolated and cloned in a multiple copy expression vector (Finnerty, W. R. and Robinson, M., Biotechnol., Bioengineer. Symp. #16, 205–221 (1986)). In these cases, C—C bonds in the benzene ring of dibenzothiophene are attacked and various water-soluble substances capable of extraction from oil are formed. During this reaction, however, other aromatic molecules in oil are also attacked and as a result a significant amount of hydrocarbons move to the liquid phase (Hartdegen, F. J., Coburn, J. M. and Roberts, R. L., Chem. Eng. Progress, 80, 63–67 (1984)). Such reaction leads to reduction in the total thermal unit in petroleum and is thus an industrially unacceptable reaction. Further, this type of microorganism for oxidative degradation of dibenzothiophene gives a water-soluble thiophene compound (mainly 3-hydroxy-2-formylbenzothiophene) as the oxidation product as reported by Kodama et al., which is, however, a substance difficult to remove from the aqueous phase.

Besides said microorganisms, certain microorganisms are known to attack a carbon skeleton in the same manner as above, to catalyze partial oxidation of organic sulfur heterocyclic compounds and to convert them into water-soluble products; examples of such microorganisms are Pseudomonas sp., *Pseudomonas aeruginosa*, Beijerinckia sp., *Pseudomonas alcaligenes, Pseudomonas stutzeri* and *Pseudomonas putida* (which catalyze partial oxidation) and Brevibacterium sp. (which catalyzes mineralization i.e. mineral formation). The genetically determinative elements of these enzyme reactions, which represent bio-transformation unique to oxidation of aromatic hydrocarbons, are believed to be generally carried on plasmids (Monticell, D. J., Bakker, D., Finnerty, W. R. Appl. Environ. Microbial, 49, 756–760 (1985)). The enzyme reactions in these microbial systems are not of sulfur-targeted types and are thus not functional for removing organic sulfur from high-molecular-weight fractions separated from crude oil, and the usefulness of the microorganisms in bio-processing of fossil fuels having a high content of sulfur is therefore limited. The reasons for this are: (1) attack on the carbon ring of dibenzothiophene occurs often at the 2- and 3-positions of dibenzothiophenes substituted with alkyl or allyl groups at said positions, and the dibenzothiophenes substituted at said positions do not serve as substrates in the Kodama pathway; (2) the pathway for destroying the carbon skeleton reduces the energy content of fuel; and (3) the major product of the pathway for destroying the carbon skeleton is 3-hydroxy-2-formylbenzothiophene, while a trace amount of dibenzothiophene is decomposed to form a sulfate, so that adequate desulfurization does not occur.

(B) C—S Bond-Targeted Type Biodesulfurization

There are reports on microorganisms degrading not only crude oil and coal but also model compounds containing sulfur so that sulfur is selectively removed as a heteroatom and sulfates and hydroxide compounds are produced. From the structures of their metabolites, these types of reactions are considered to be reactions in which C—S bonds in sulfur compounds are specifically cleaved and as a result the sulfur is released in the form of sulfate. Aerobic and heterotrophic non-acidophilic soil microorganisms Pseudomonas CB1 and Acinetobacter CB2 were reported to convert thiophene sulfur into sulfate (Isbister, J. D. and Kobylinski, E. A. (Microbial desulfurization of coal. in Coal Science and Technology, Ser. 9, p. 627 (1985). When a bench-scale continuous bioreactor was used, the content of organic sulfur in Illinois #6 coal was reduced 47% by use of CB1. Dibenzothiophene sulfoxide, dibenzothiophene sulfone, 2,2'-dihydroxybiphenyl have been identified as intermediates of dibenzothiophene in desulfurization. Separately, it has been reported that 35 to 45% of the organic sulfur content in 4 different types of coal is removed as sulfates by unidentified microorganisms isolated from soil (Finnerty, W. R. and Robinson, M., Biotechnol. Bioengineer. Symp. #16, 205–221 (1986)). In addition, an isolated strain, *Rhodococcus rhodochrous* ATCC53968, has a sulfur-targeted type pathway for converting dibenzothiophene into hydroxybiphenyl and sulfate, and it is said that 70% of the organic sulfur content in crude oil and coal is reduced by this microorganism (Kilbane, J. J. Resources, Conservation and Recycling, 3, 69–70 (1990)). For Corynebacterium sp., there is also a description of a pathway for degrading dibenzothiophene by similarly oxidizing dibenzothiophene and converting it via dibenzothiophene sulfoxide, then dibenzothiophene sulfone, into 2-hydroxybiphenyl and sulfate (Ohmori, T., Monna, L., Saiki, Y. and Kodama, T. Appl. Environ. Microbiol., 58, 911–915, 1992). In this case, the 2-hydroxybiphenyl is further converted into nitrates to form 2 different hydroxy nitrobiphenyls. Recently, there are also reports on oxidation of dibenzothiophene into benzoic acid and nitrite by Brevibacterium sp. DO (van Afferden. M., Schacht, S., Klein, J. and Truper, H. G. Arch. Microbiol., 153, 324–328, 1990) and oxidation of benzyl methyl sulfide into benzaldehyde by Pseudomonas sp. OS1 (van Afferden, M., Tappe, D., Beyer, M., Truper, H. G. and Klein, J. Fuel72, 1635–1643, 1993). Arthrobacter K3b has been reported to exhibit a reaction similar to that of the brevibacterium, and when dibenzothiophene sulfone is used as a substrate, sulfite and benzoic acid are produced (Dahiberg, M. D. (1992) Third International Symposium on the Biological Processing of Coal, May 4–7, Clearwater Beach, Fla., pp. 1–10, Electric Power Research Institute, Palo Alto, Calif.). Meanwhile, a novel system has also been reported in which conversion of a sulfur-containing aromatic heterocyclic compound into hydrogen sulfide is carried out in a non-aqueous solvent (Finnerty, W. R. Fuel72, 1631–1634, 1993). An unidentified strain FE-9 converts dibenzothiophene into biphenyl and hydrogen sulfide in 100% dimethylformamide in a hydrogen atmosphere or into hydroxybiphenyl and sulfate in the presence of air. This strain is further reported to convert thianthrene into benzene and hydrogen sulfide in a hydrogen atmosphere or into benzene and sulfates in the presence of air. Besides such microorganisms aerobically degrading dibenzothiophene, anaerobic and sulfate-reducing microorganisms are also reported to convert dibenzothiophene into biphenyl and hydrogen sulfide and to convert petroleum organic sulfur biologically into hydrogen sulfide (Kim, H. Y., Kim, T. S. and Kim, B. H., Biotechnol. Lett. 12, 757–760, 1990a; Kim, T. S., Kim, H. Y. and Kim, B. H., Biotechnol. Lett. 12, 761–764, 1990b). The C—S bond-targeted type bio-desulfurizing microorganisms as described above are summarized as follows:

petroleum fraction to normal temperature. There are the following reports on high-temperature biodesulfurization.

Most of the attempts at desulfurization by microorganisms at high temperature can be found in coal desulfurization. A variety of sulfur compounds are contained in coal. The major inorganic sulfur compound is iron pyrite, while the organic sulfur compound is present in the form of a mixture of a wide variety of organic sulfur compounds, many of which are known to contain thiol, sulfide, disulfide and thiophene groups. The microorganisms used are those of the genus Sulfolobus, all of which are thermophilic microorganisms. There are reports in which a wide variety of Sulfolobus strains have been used for leaching of metals from mineral sulfide (Brierley C. L. & Murr, L. E., Science 179, 448–490 (1973)) and removal of sulfur from iron pyrite in coal (Kargo, F. & Robinson, J. M., Biotechnol. Bioeng. 24, 2115–2121 (1982); Kargi, F. & Robinson, J. M., Appl. Environ. Microbiol., 44, 878–883 (1982); Kargi, F. & Gervoni. T. D., Biotechnol. Letters 5, 33–38 (1983); Kargi, F. and Robinson, J. M., Biotechnol. Bioeng., 26, 687–690 (1984); Kargi, F. & Robinson, J. M., Biotechnol. Bioeng. 27,

TABLE 1

C-S Bond Attack Type Microorganisms

| Strain | Substrate | Degradation Product | Literature |
|---|---|---|---|
| *Pseudomonas sp.* CB1 | dibenzothiophene; coal | hydroxybiphenyl + sulfate | Isbister et al. (1985) |
| *Acinetobacter sp.* CB2 | dibenzothiophene | hydroxybiphenyl + sulfate | Isbister et al. (1985) |
| Gram-positive bacteria | coal | sulfate | Crawford et al. (1990) |
| *Rhodococcus rhodochrous* IGTS8 (ATCC 53968) | dibenzothiophene; coal, petroleum | hydroxybiphenyl + sulfate | Kilbane (1989) |
| *Desulfovibrio desulfuricans* | dibenzothiophene | biphenyl + hydrogen sulfide | Kim et al. (1990) |
| *Corynebacterium sp.* | dibenzothiophene | hydroxybiphenyl + sulfate | Omori et al. (1992) |
| *Brevibacterium sp.* DC | dibenzothiophene | benzoic acid + sulfite | van Alferden et al. (1990) |
| Gram-positive bacterium FE-9 | dibenzothiophene; thianthrene | biphenyl + hydrogen sulfide benzene + hydrogen sulfide | Finnerty (1993) |
| *Pseudomonas sp.* OS1 | benzylmethylsulfide | benzaldehyde | van Afferden (1993) |
| *Rhodococcus erythropolis* | dibenzothiophene | hydroxybiphenyl | Wang. et al. (1994) |
| *Rhodococcus erythropolis* D-1, H-2 | dibenzothiophene | hydroxybiphenyl | Izumi et al. (1994) Ohshiro et al. (1995) |
| *Agrobacterium sp.* | dibenzothiophene | hydroxybiphenyl | Constanti et al. (1994) |
| *Xanthomanas sp.* | dibenzothiophene | hydroxybiphenyl | Constanti et al. (1994) |
| Arthrobacter K3b | dibenzothiophene | benzoic acid + sulfite | Dahlberg (1992) |

(C) Conventional High-Temperature Biodesulfurization Methods

Microbial metabolic reaction proceeding at a temperature of about 30° C. is utilized in every biodesulfurization described above. On the other hand, it is known that the rate of chemical reaction increases generally depending on temperature. In the desulfurization step in a petroleum refining process, fractional distillation and desulfurization reaction are carried out under high-temperature and high-pressure conditions. For incorporating a biodesulfurization step into a petroleum refining process, therefore, it is considered desirable that the biodesulfurization reaction can be carried out at higher temperature during cooling, without cooling a 41–49 (1985); Kargi, F., Biotechnol. Lett., 9, 478–482 (1987)). According to Kargi and Robinson (Kargi. F. and Robinson, J. M., Appl. Environ. Microbiol., 44, 878–883 (1982)), a certain strain *Sulfolobus acidocaldarius* isolated from an acidic hot spring in the Yellow Stone National Park, US, grows at 45 to 70° C. and oxidizes elementary sulfur at optimum pH 2. Further, oxidation of iron pyrite by other 2 *Sulfolobus acidocaldarius* strains has also been reported (Tobita, M., Yokozeki, M., Nishikawa, N. & Kawakami, Y., Biosci. Biotech. Biochem.58, 771–772 (1994)).

Among the organic sulfur compounds contained in fossil fuels, dibenzothiophene and its substituted derivatives are known to hardly undergo hydrodesulfurization in a petroleum refining process. High-temperature degradation of dibenzothiophene by *Sulfolobus acidocaldarius* has also been reported (Kargi, K. & Robinson, J. M., Biotechnol. Bioeng.26, 687–690 (1984); Kargi, F., Biotechnol. Letters 9, 478–482 (1987)). According to these reports, if model aromatic heterocyclic sulfur compounds such as thianthrene, thioxanthene and dibenzothiophene were reacted at high temperature with this microorganism, these sulfur compounds were oxidized and decomposed. The oxidation of these aromatic heterocyclic sulfur compounds by *S. acidocaldarius* has been observed at 70° C., and sulfate ion is formed as the reaction product. However, this reaction was carried out in a medium not containing a carbon source except for the sulfur compound. Therefore, this sulfur compound can also be used as a carbon source by this organism. That is, C—C bonds in the sulfur compound are evidently decomposed. Further, this microorganism *Sulfolobus acidocaldarius* can grow only in an acidic medium, so the oxidative degradation of dibenzothiophene by this microorganism is required to proceed under severe acidic conditions (pH 2.5). Such severe conditions are considered undesirable for the process because deterioration of petroleum products are caused under such conditions and simultaneously acid-resistant materials are required for the desulfurization step. If *Sulfolobus acidocaldarius* is allowed to grow under autotrophic conditions, it derives necessary energy from reduced iron and sulfur compounds and utilizes carbon dioxide as a carbon source. If *Sulfolobus acidocaldarius* is allowed to grow under heterotrophic conditions, it can utilize a wide variety of organic compounds as both carbon and nitrogen sources. Namely, if fossil fuels are present, these would be assimilated as a carbon source by the microorganism.

Finnerty et al. have reported that strains belonging to *Pseudomonas stutzeri*, *Pseudomonas alcaligenes* and *Pseudomonas putida* decompose dibenzothiophene, benzothiophene, thioxanthene and thianthrene to convert them into water-soluble substances (Finnerty, W. R., Shockiey, K., Attaway, H. in Microbial Enhanced Oil Recovery, zajic, J. E. et al. (eds.) Penwell. Tulsa, Okla., 83–91 (1983)). The oxidation reactions in these cases are assumed to proceed even at 55° C. However, the degradation product of dibenzothiophene by these Pseudomonas strains was 3-hydroxy-2-formylbenzothiophene as reported by Kodama et al. (Monticello, D. J., Bakker, D., Finnerty, W. R. Appl. Environ. Microbiol., 49, 756–760 (1985)). The activity of these Pseudomonas strains in oxidizing dibenzothiophene is induced by naphthalene or salicylic acid i.e. a sulfur-free aromatic hydrocarbon while inhibited by chloramphenicol. As can be seen from this, the degradation reaction of dibenzothiophene by the Pseudomonas strains is based on the degradation by cleavage of C—C bonds in an aromatic ring. Thus, their degradation can occur not only in sulfur compounds but also in important aromatic hydrocarbons contained in petroleum fractions, resulting in reduction in the value of the fuel as well as the qualities of the petroleum fractions.

The microorganisms so far found to be capable of degrading dibenzothiophene at high temperatures catalyze cleavage of C—C bonds in a dibenzothiophene molecule and utilize it as a carbon source. As described above, the degradation reaction of organic sulfur compounds, in which C—S bonds are specifically cleaved while C—C bonds are not cleaved and remain, are desirable for actual petroleum desulfurization methods as discussed above (Conventional Biodesulfurization Methods). That is, the use of microorganisms having the activity of cleaving C—S bonds in dibenzothiophene and its alkyl substituted molecules at high temperatures and forming desulfurization products in the form of water-soluble substances is most preferable for the biodesulfurization process.

As described above, microorganisms in some genera are known to exhibit C—S-bond-cleavage-type degradation reactions against dibenzothiophene. However, there is no description that such microorganisms demonstrated the activity of degrading dibenzothiophene under high-temperature conditions at 42° C. or more. For example, Rhodococcus sp. ATCC 53968 is a well examined dibenzothiophene-degrading strain, and by the reaction of this microorganism, an oxygen atom is added to the sulfur atom of dibenzothiophene, and the resulting dibenzothiophene sulfoxide is converted into dibenzothiophene sulfone which via 2'-hydroxybiphenyl-2-sulfinate, is further converted into 2-hydroxybiphenyl. However, the growth of this microorganism in 48 hour culture is also significantly delayed or prevented at 43° C. or even at 37° C. slightly higher than the usual culture temperature of 30° C. (Unexamined Published Japanese Patent Application No. 6-54695). It is therefore considered the most suitable for high-temperature desulfurization to use a microorganism capable of growing at high temperatures and degrading organic sulfur compounds, particularly heterocyclic sulfur compounds such as dibenzothiophene and its substituted derivatives by specifically cleaving C—S bonds in said compounds.

SUMMARY OF THE INVENTION

As described above, the microorganisms used in the step of desulfurizing petroleum are preferably those capable of growing at high temperatures and specifically cleaving C—S bonds in an organic sulfur compound, but none of such microorganisms have been found. The present invention was made under such a technical background, and the object of the present invention is to isolate, from nature, a microorganism capable of growing at high temperatures and specifically cleaving C—S bonds in order to provide a means of desulfurizing petroleum etc. by use of said microorganism.

As a result of their eager study, the present inventors found that several kinds of strains belonging to the genus Paenibacillus can grow under high-temperature conditions and can specifically cleave C—S bonds in organo sulfur compounds, so that the present invention was completed.

That is, the present invention relates to a method of degrading organic sulfur compounds, in which organic sulfur compounds are decomposed by a microorganism having the ability to decompose organic sulfur compounds.

Further, the present invention relates to Paenibacillus sp. A11-1 and Paenibacillus sp. A11-2 having the ability to decompose organic sulfur compounds at high temperatures.

DETAILED DESCRIPTION OF THE INVENTION

Figure 1:
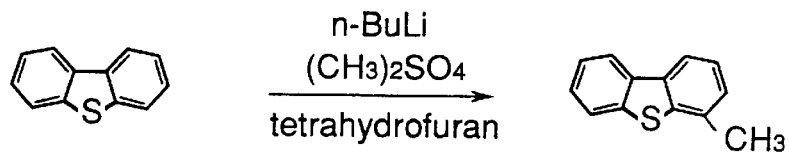
FIG. 1 shows the methods for chemical synthesis of various methyl derivatives of dibenzothiophene.
Figure 1:
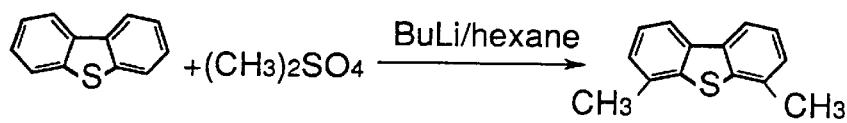
Figure 1:
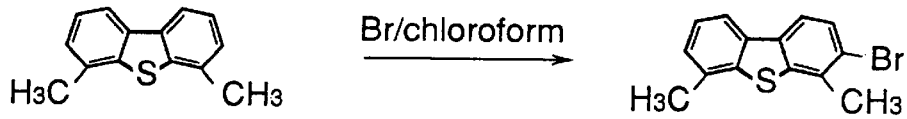
Figure 1:
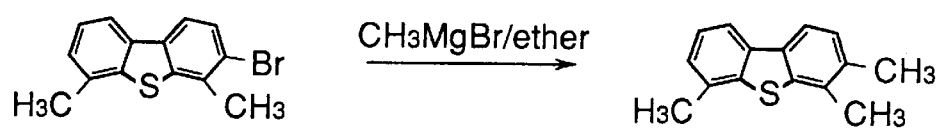

Hereinafter, the present invention is described in detail.

First, the A11-1 and A11-2 strains of the present invention are described.

The A11-1 and A11-2 strains were found by the present inventors through screening many types of soil collected as microbial sources in various places in Japan. The A11-1 and A11-2 strains have the following microbiological properties:

|  | A11-1 strain 0.5 to 0.7 μm wide 2.5 to 5.0 μm long | A11-2 strain 0.5 to 0.7 μm wide 2.5 to 5.0 μm long |
| --- | --- | --- |
| form of cells | | |
| formation of spores | + | + |
| form of spores | elliptical | elliptical |
| catalase test | + | + |
| VP reaction | − | − |
| pH of VP medium | 5.5 | 5.5 |
| optimal growth temperature | 60° C. | 60° C. |
| growth at pH 5.7 | − | − |
| growth in the presence of 2% common salt | + | + |
| growth in the presence of 5% common salt | − | − |
| growth in the presence of 7% common salt | − | − |
| growth in the presence of 10% common salt | − | − |
| acid formation from D-glucose | + | + |
| acid formation from L-arabinose | + | + |
| acid formation from D-xylose | + | − |
| gas generation from glucose | − | − |
| lecithinase production | − | − |
| hydrolysis of starch | + | + |
| hydrolysis of gelatin | − | − |
| hydrolysis of casein | − | − |
| hydrolysis of aesculin | − | − |
| utilization of citric acid | − | − |
| utilization of propionic acid | − | − |
| degradation of tyrosine | − | − |
| sulfite formation from nitrate | − | − |
| indole formation | − | − |
| phenylalanine deaminase activity | − | − |
| arginine dihydrolase activity | − | − |
| urease test | − | − | partial sequence of 16S rDNA: Both the A11-1 and A11-2 strains have the maximum homology of 91 to 92% to microorganisms belonging to Paenibacillus in respect of a partial sequence of 16S rDNA.

As a result of their examination of said microbiological properties in light of the microbiological properties described by Ash et al. in Antonie van Leeuwenhock 64, 253–260 (1993), the present inventors identified both A11-1 and A11-2 as belonging to the genus Paenibacillus, but among the known species belonging to the genus Paenibacillus, there were no microorganisms whose properties were in complete agreement with the above microbiological properties. Hence, the A11-1 and A11-2 strains were designated Paenibacillus sp. A11-1 and A11-2, respectively. These strains were deposited as FERM BP-6025 on Jul. 22, 1995 and FERM BP-6026 on Jul. 22, 1995 with the National Institute of Bioscience and Human-Technology, Agency of Industrial Science and Technology, Japan. In 1991, Ash et al. classified the microorganisms of the Bacillus group into 5 groups i.e. rRNA Groups 1 to 5 according to the sequence of 16S rRNA gene (Ash, C., Farrow, J. A. E., Wallbands, S. and Collins M. D., Lett. Appl. Microbiol., 13, 202–206 (1991)). They further divided rRNA Group 3 extremely homologous to each other in the 16S rRNA gene into one independent genus named Paenibacillus. Microbial species conventionally classified as belonging to the genus Bacillus and newly classified as belonging to the genus Paenibacillus include *Bacillus alvei, B. amylolyticus, B. azotofixans, B. gordonae, B. larvae, B. macerans, B. macquariensis, B. pabuli, B. polymyxa, B. pulvifaciens and B. validus*. It has been confirmed that the microorganisms of the Paenibacillus can be easily distinguished from other microorganisms of the genus Bacillus by blotting analysis using a highly specific gene probe based on the 16S rRNA and by sequencing the 16S rRNA gene (Ash, C., Priest, F. G., Collins, M. O., Antonie van Leeuwenhock 64, 253–260 (1993)).

A11-1 and A11-2 are cultured according to the conventional culturing methods. They are cultured preferably in a liquid medium. Any conventional sources can be used as nutrient sources in this medium. The carbon source may be any utilizable carbon compounds such as glucose, sucrose, lactose, fructose, ethanol, etc. The nitrogen source may be any utilizable nitrogen compounds, and organic nutrient substances such as peptone, polypeptone, meat extract, yeast extract, soybean powder, casein hydrolysate, etc. can also be used. If it is desired to use a medium not containing any sulfur compound which can affect desulfurization, inorganic nitrogen compounds such as ammonium chloride etc. can also be used. In addition, phosphates, carbonates, magnesium, calcium, potassium, sodium, iron, manganese, zinc, molybdenum, tungsten, copper, vitamins, etc. are used as necessary. Culturing is carried out for 1 or 2 days, at pH 6 to 8 and at a temperature of 37 to 60° C. under aerobic conditions with shaking or aeration.

Hereinafter, the method of degrading organic sulfur compounds according to the present invention is described.

The method of degrading organic sulfur compounds according to the present invention is carried out using a microorganism. Examples of microorganisms used herein are A11-1 and A11-2, but any microorganisms belonging to the genus Paenibacillus having the ability to decompose organic sulfur compounds may be used.

In the present invention, typical but nonrestrictive examples of organic sulfur compounds are heterocyclic organic sulfur compounds. The heterocyclic organic sulfur compounds include, e.g. benzothiophene, dibenzothiophene and their substituted derivatives. Examples of such substituted derivatives include, but are not limited to, alkyldibenzothiophenes, more specifically 4-methyldibenzothiophene, 4,6-dimethyldibenzothiophene, 2,8-dimethyldibenzothiophene, 3,4,6-trimethyldibenzothiophene, etc.

As a specific degradation method, mention may be made of a method of culturing the microorganism in a liquid containing an organic sulfur compound (growing cell method), a method of contacting the microorganism with a solution containing an organic sulfur compound (resting cell method), etc.

The growing cell method can be carried out e.g. as follows:

The degradation of organic sulfur compounds can be carried out by culturing the microorganism under shaking or rotation at 50° C. after inoculating a suitable amount (e.g., 1 to 2% by volume) of a stock of the microorganism into a fresh medium containing a suitable organic sulfur compound. The microorganism inoculated is preferably in the logarithmic growth late phase but may be in any phase between the initial logarithmic growth phase and the stationary phase. The volume of the microorganism inoculated may be varied as necessary. The medium is preferably a high-temperature desulfurization medium, but any other medium can be used. Any conventional sources are used as nutrient sources in the medium. The carbon source may be any utilizable carbon compounds such as glucose, sucrose, lactose, fructose, ethanol etc. The nitrogen source may be any utilizable nitrogen compounds, and organic nutrient substances such as peptone, polypeptone, meat extract, yeast extract, soybean powder, casein hydrolysate etc. can also be used. If it is desired to use a medium not containing any sulfur compounds which can affect desulfurization, inorganic nitrogen compounds such as ammonium chloride etc. can also be used in place of said organic nutrient substances. In addition, phosphates, carbonates, magnesium, calcium, potassium, sodium, iron, manganese, zinc, molybdenum, tungsten, copper, vitamins, etc. are used as necessary. Culture is carried out for 1 or 2 days at 50° C. under aerobic conditions with shaking or aeration. The culture temperature is preferably 50° C., but an arbitrary temperature of 37 to 60° C. may also be used. The culture period may also be varied as necessary.

The liquid containing organic sulfur compounds may be not only fractions such as crude oil, heavy oil, light gas oil, kerosene, gasoline, etc., but also any liquid containing organic sulfur compounds.

The concentration of the organic sulfur compounds in this liquid is preferably 50 to 500 ppm but may be varied as necessary. Before the liquid containing organic sulfur compounds is added, the culture liquid may be preliminarily heated to the same temperature as the reaction temperature. The degradation of organic sulfur compounds by the growing cell method using the high-temperature desulfurizing microorganism of the present invention may be conducted in 2 (oil/water) phases containing an organic solvent such as tetradecane. In this case, the organic solvent used may be not only tetradecane but also kerosine, light gas oil, heavy gas oil etc. as well as hydrocarbons which are in the form of a liquid at the reaction temperature. If necessary, the gas phase over the culture liquid may be replaced by oxygen. Further, air or oxygen may be introduced into the culture liquid.

The resting cell method can be carried e.g. as follows:

The preparation of the microorganism can be carried out by culturing the microorganism by shaking or rotation at 50° C. after inoculating a suitable amount (e.g. 1 to 2% by volume) of a stock of the microorganism into a fresh medium. The microorganism inoculated is preferably in the later logarithmic growth phase but may be in any phase between the initial logarithmic growth phase and the stationary phase. The volume of the microorganism inoculated may be varied as necessary. The medium is preferably a high-temperature desulfurization medium, but any other medium can be used. Any conventional sources are used as nutrient sources in the medium. The carbon source may be any utilizable carbon compounds such as glucose, sucrose, lactose, fructose, ethanol, etc. The nitrogen source may be any utilizable nitrogen compounds, and organic nutrient substances such as peptone, polypeptone, meat extract, yeast extract, soybean powder, casein hydrolysate, etc. can also be used. If it is desired to use a medium not containing any sulfur compounds which can affect desulfurization, inorganic nitrogen compounds such as ammonium chloride etc. can also be used. In addition, phosphates, carbonates, magnesium, calcium, potassium, sodium, iron, manganese, zinc, molybdenum, tungsten, copper, vitamins, etc. are used as necessary. Culturing is carried out for 1 or 2 days at 50° C. under aerobic conditions with shaking or aeration. The culturing temperature is preferably 50° C., but an arbitrary temperature of 37 to 60° C. may also be used.

The microorganism thus cultured is separated and collected by means such as centrifugation etc. Preferably, the microorganism is washed and collected again for use in the resting cell reaction. In this case, the microorganism is collected in the middle logarithmic growth to later phase, but the microorganism in the initial logarithmic growth phase to the stationary phase can also be used. As a means of separating and collecting the microorganism, any means such as filtration and sedimentation separation besides centrifugation may be used. To wash the microorganism, physiological saline as well as any buffers such as phosphate buffer, Tris buffer, etc. may be used, and water can also be used to wash the microorganism.

The resting cell reaction is carried out by adding a liquid containing organic sulfur compounds to a microbial suspension prepared by suspending the microorganism in a suitable buffer. As the buffer, various buffers can be used. The buffer is preferably at pH 6 to 7 but may be at any pH value. Water, medium, etc. may be used in place of the buffer. The concentration of the microbial suspension is preferably between 1 and 50 in terms of $OD_{660}$ but may be varied as necessary.

The liquid containing organic sulfur compounds may be not only fractions such as crude oil, heavy gas oil, light gas oil, kerosene, gasoline, etc., but also any liquid containing organic sulfur compounds.

The concentration of the organic compounds in this liquid is preferably 50 to 500 ppm but may be varied as necessary. Before the liquid containing organic sulfur compounds is added, the reaction liquid may be preliminarily heated to the same temperature as the reaction temperature. The resting cell reaction is carried out preferably at 50° C. but any temperature of 37 to 60° C. can be used. The reaction time is preferably 1 to 2 hours but can be varied as necessary. Further, the resting cell reaction may be carried out in a 2-phase (oil/water) system to which an organic solvent such as tetradecane etc. has been added. In this case, the organic solvent used may be not only tetradecane but also kerosine, light gas oil, heavy gas oil, etc., as well as hydrocarbons which are in the form of a liquid at the reaction temperature. If necessary, the gas phase over the culture liquid may be replaced by oxygen.

The degradation method of the present invention can be carried out as described above, and the reaction product formed by degradation can be extracted and analyzed in e.g. the following manner.

After adjusted to pH 2 or thereabout with 6 N hydrochloric acid, the reaction solution is stirred and extracted with ethyl acetate. However, the solvent used for extraction is not limited to ethyl acetate, and any solvent can be used insofar as the desired reaction product can be extracted. The amount of ethyl acetate is preferably equal to the volume of the reaction but can be varied as necessary. The separation of the reaction product can be effected using a reverse phase C18 column or normal phase silica column, but other columns may also be used as necessary.

The separation method is not limited to those described above, and any methods can be used insofar as the reaction product can be separated. The analysis of the reaction products can be done using gas chromatography, gas chromatography/mass spectrometry, gas chromatography/ atomic emission spectrometry, gas chromatography/Fourier transformation infrared spectrometry, nuclear magnetic resonance, etc. If necessary, other analytical methods can be used in combination. The analytical method is not limited to these methods, and any methods can be used if the reaction products can be analyzed.

According to the present invention, heterocyclic ring-containing sulfur compounds can be decomposed by specifically cleaving its C—S bonds under considerably higher temperature conditions than those conventionally feasible. According to the present invention, heterocyclic organic sulfur compounds such as benzothiophene, dibenzothiophene and alkyldibenzothiophenes contained in fossil fuels can be decomposed by specifically cleaving their C—S bonds under considerably more moderate conditions than in current hydrodesulfurizati on but at considerably higher temperature than in the conventional microbial desulfurization, so that effective desulfurization is made feasible.

EXAMPLES

Hereinafter, the present invention is described in more detail with reference to the Examples.

Example 1
Isolation of Microorganisms Degrading Dibenzothiophene at High Temperatures The microorganism for high-temperature desulfurization was isolated as follows: The medium (high-temperature desulfurization medium) shown in Table 2, which contains as a sole sulfur source dibenzothiophene, i.e., a typical organic sulfur compound contained in a petroleum fraction, was used for the enrichment and isolation of the desired desulfurizing microorganism. First, 5 ml of the high-temperature desulfurization medium was introduced into a test tube with a stopper (27 ml volume, 18 mm diameter× 180 mm length), and about 0.5 g soil collected from various places in Japan was added to via a spatula to it and cultured at 50° C. for 2 to 3 days with stirring at 120 r.p.m. so that microorganisms were enriched. If the culture medium became turbid, 0.1 ml of the culture medium was added to a fresh medium with the same composition and this operation was repeated 3 or 4 times. The microorganisms thus grown were then cultured in the high-temperature desulfurization medium. The resulting culture (2.5 ml) was placed in a test tube with a stopper and 6 N hydrochloric acid was added dropwise to it to adjust the pH to 2.5 or less, and the products were extracted by stirring with an equal volume of ethyl acetate. The extracted products were analyzed by gas chromatography, and if 2-hydroxybiphenyl was found to be formed, the microorganisms in the corresponding culture was then isolated in the following procedure.

The culture in which 2-hydroxybiphenyl had been formed was diluted with the high-temperature desulfurization medium. The dilutions thus obtained were plated on an agar plate containing 2% agar and grown at 50° C. in stationary culture to form colonies. A part of the formed colonies were inoculated into the high-temperature desulfurization medium and cultured in the liquid medium in the same manner as above. The formation of 2-hydroxybiphenyl in the resulting culture was examined in the same manner as above. The colonies which had formed 2-hydroxybiphenyl were selected and a series of the operations described above were repeatedly carried out 2 or 3 times so that the desired strains were isolated.

TABLE 2

| Composition for High-Temperature Desulfurization Medium | |
| --- | --- |
| glucose | 5.0 g |
| $K_2HPO_4$ | 4.0 g |
| $KH_2PO_4$ | 0.5 g |
| $NH_4Cl$ | 1.0 g |
| $MgCl_2$ | 0.2 g |
| metal solution | 10 ml |
| vitamin solution | 1 ml |
| yeast extract | 50 mg |
| dibenzothiophene | 100 mg |
| pH | 7.5 |
| distilled water | 1000 ml |
| Metal Solution | |
| NaCl | 1 g |
| $CaCl_2$ | 2 g |
| $FeCl_2 \cdot 4H_2O$ | 0.5 g |
| $ZnCl_2$ | 0.5 g |
| $MnCl_2 \cdot 4H_2O$ | 0.5 g |
| $CuCl_2$ | 0.05 g |
| $Na_2MoO_4 \cdot 2H_2O$ | 0.1 g |
| $Na_2WO_4 \cdot 2H_2O$ | 0.05 g |
| distilled water | 1000 ml |
| Vitamin Solution | |
| calcium pantothenate | 400 mg |
| inositol | 200 mg |
| nicotinic acid | 400 mg |
| p-aminobenzoic acid | 200 mg |
| pyridoxine hydrochloride | 400 mg |
| cyanocobalamine | 0.5 mg |
| distilled water | 1000 ml |

Example 2

High-Temperature Degradation of Dibenzothiophene by Microorganism

The high-temperature desulfurization medium containing an organic sulfur compound dibenzothiophene as a sole sulfur source was used in an attempt to culture the desulfurizing strain at various temperatures, and the degradation of dibenzothiophene was evaluated using microbial growth and 2-hydroxybiphenyl formation as the indicator.

Five milliliters of the high-temperature desulfurization medium described in Example 1 was introduced into a test tube with a stopper and preheated at a predetermined temperature for a predetermined time, and then each of the precultures prepared in the same manner as in Example 1 was added thereto at a final concentration of 2% and a degradation test was conducted under the culture conditions described in Example 1. The turbidity of each culture at 660 nm was determined in a spectrophotometer, and this turbidity was used to evaluate the degree of growth of the microorganism. The degradation products were analyzed by gas chromatography in the same manner as in Example 1 and the amount of 2-hydroxybiphenyl formed was determined. The results of the degradation of dibenzothiophene by the high-temperature desulfurizing strain Paenibacillus sp. A11-2 are shown in Table 3.

TABLE 3

Degradation of Dibenzothiophene by the High-Temperature Desulfurizing Microorganism at Each Temperature

| Temp. (°C.) | Degree of Growth (OD660) | Amount of Formed 2-Hydroxybiphenyl (ppm) |
|---|---|---|
| 65 | 0 | 3.1 |
| 58 | 1.32 | 43.7 |
| 54 | 1.04 | 35.7 |
| 51 | 1.18 | 37.7 |
| 48 | 0.86 | 26.0 |
| 45 | 0.96 | 28.4 |
| 42 | 0.88 | 22.7 |
| 39 | 0.54 | 8.5 |
| 36 | 0.38 | 3.6 |
| 33 | 0.14 | 3.0 |
| 30 | 0.06 | 2.9 |

As is evident from the result shown in Table 3, at least in the range of 33 to 58° C. there occurs the significant growth of the desulfurizing microorganism, which is accompanied by degradation of dibenzothiophene. Both the degree of growth in the high temperature range of 51 to 58° C. and the degree of formation of 2-hydroxybipheneyl are particularly higher than those in the lower temperature range. That is, the high-temperature desulfurizing microorganism described in the present invention can perform desulfurization effectively depending on high temperature.

Example 3
High-Temperature Degradation of Dibenzothiophene Derivatives

The desulfurizing strain was grown in the high-temperature desulfurization medium containing alkyl derivatives of dibenzothiophene as a sole sulfur source, and its ability to decompose these dibenzothiophene derivatives was examined. As the alkyl derivatives, 4-methyldibenzothiophene (A), 4,6-dimethyldibenzothiophene (B), 2,8-dimethyldibenzothiophene (C), and 3,4,6-trimethyldibenzothiophene (D) were used. To confirm that the alkyl derivatives of dibenzothiophene were decomposed by the high-temperature desulfurization strain in the coexistence of a hydrocarbon-type solvent actually contained in petroleum, each dibenzothiophene derivative was dissolved in n-tetradecane to prepare a solution containing 100 ppm sulfur, and this solution was added to the high-temperature desulfurization medium. Because Compounds (A), (B) and (D) were reagents not commercially available, these were synthesized according to the schemes as shown in (1) to (3) in FIG. 1.

Ten milliliters of the medium and 2 ml of the n-tetradecane containing organic sulfur compound were introduced into a 100 ml Erlenmeyer flask equipped with a stopper, and each of pre-cultured microbial cultures prepared as described in Example 1 was inoculated thereinto at a concentration of about 1% and cultured at 50° C. with stirring 120 r.p.m. The turbidity of each culture at 660 nm was determined in a spectrophotometer, and this turbidity was used to evaluate the degree of growth of the microorganism. To analyze the total sulfur content in the culture, a part of the tetradecane phase was separated from water by centrifuging the culture and analyzed for its sulfur content in the Anteck Model 7000S sulfur analyzer using a pyro-ultraviolet fluorescence method. As the control, the microorganism was grown simultaneously in the medium not containing the sulfur compound. The results of the degradation of the dibenzothiophene derivatives by the high-temperature desulfurizing strain Paenibacillus sp. A11-2 are shown in Table 4.

TABLE 4

Degradation of Dibenzothiophene Derivatives by the High-Temperature Desulfurizing Microorganism

| Dibenzothiophene Derivatives | Degree of Growth (OD660) | Degree of Desulfurization (%) |
|---|---|---|
| Control | 0 | 0.0 |
| 4-methyldibenzothiophene | 1.56 | 26.0 |
| 4,6-dimethyldibenzothiophene | 1.15 | 25.5 |
| 2,8-dimethyldibenzothiophene | 1.77 | 23.5 |
| 3,4,6-trimethyldibenzothiophene | 1.20 | 29.5 |

As shown in Table 4, the growth of the desulfurizing microorganism was accompanied by degradation of the dibenzothiophene derivatives in the coexistence of the hydrocarbon type solvent contained in petroleum, and there occurred 20 to 30% reduction in the sulfur content. In this example, it was revealed that the dibenzothiophene derivatives were desulfurized efficiently as the desulfurizing microorganism grew.

Further, the desulfurization products were extracted from the decane layer through a solid-phase extraction cartridge column (Bond Elut produced by Barian) and analyzed by gas chromatography and gas chromatography/mass spectrometry. The molecular weights of the degradation products of the respective dibenzothioppene derivatives by the high-temperature desulfurizing microorganism were estimated by mass spectra obtained in gas chromatography/mass spectrometry and the results are shown in Table 5. It is estimated from Table 5 that a sulfur atom is specifically removed from each of the organic sulfur compounds, and various hydroxylated compounds corresponding to 2-hydroxybiphenyl as the degradation product of dibenzothiophene have been formed.

TABLE 5

Degradation Products of Dibenzothiophene Derivatives by High-Temperature Desulfurizing Microorganism

| Dibenzothiophene | Molecular Weight of Product |
|---|---|
| 4-methyldibenzothiophene | 184 |
| 4,6-dimethyldibenzothiophene | 198 |
| 2,8-dimethyldibenzothiophene | 198 |
| 3,4,6-trimethyldibenzothiophene | 212 |

Figure 2:
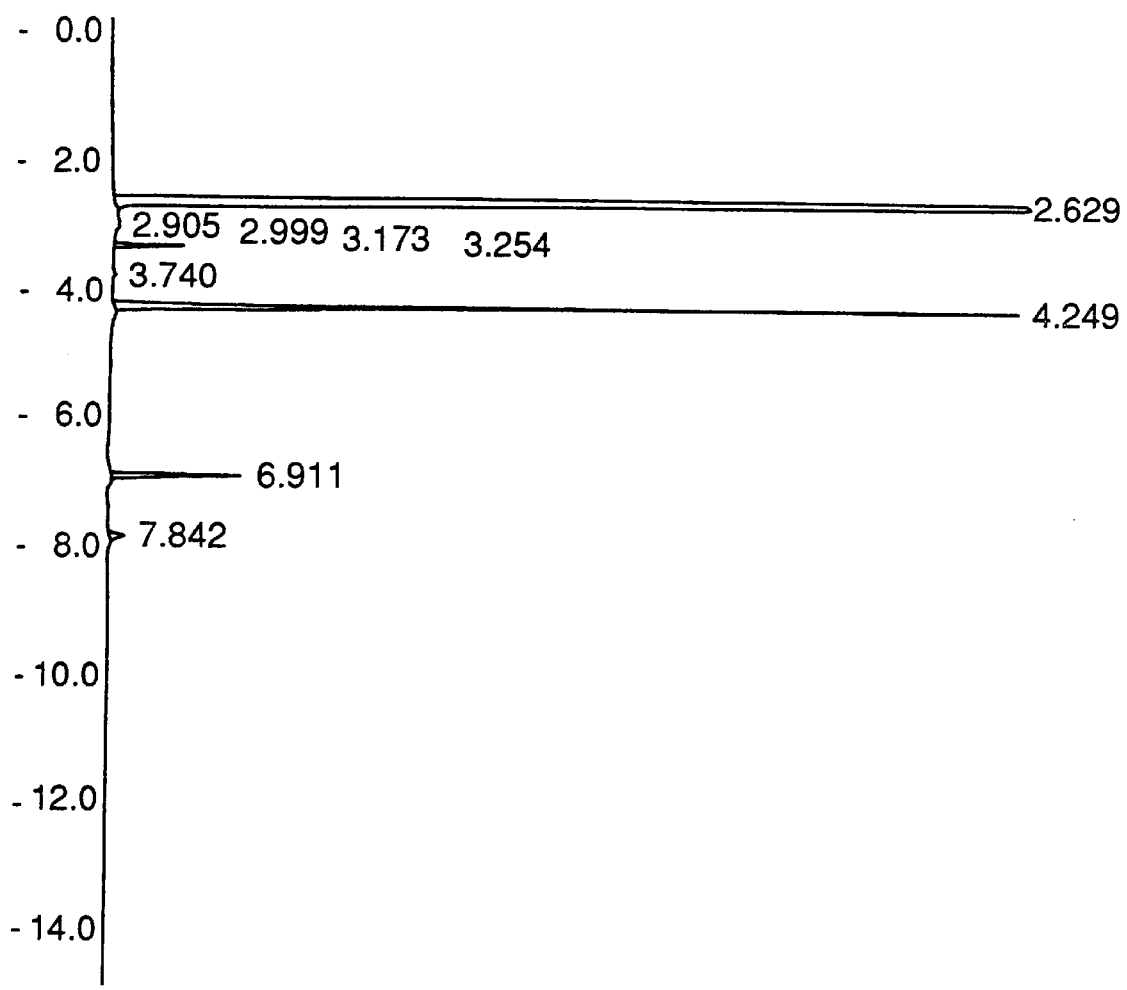
FIG. 2 shows a gas chromatogram of high-temperature desulfurization products of 4,6-dimethylbenzothiophene.
Figure 3:
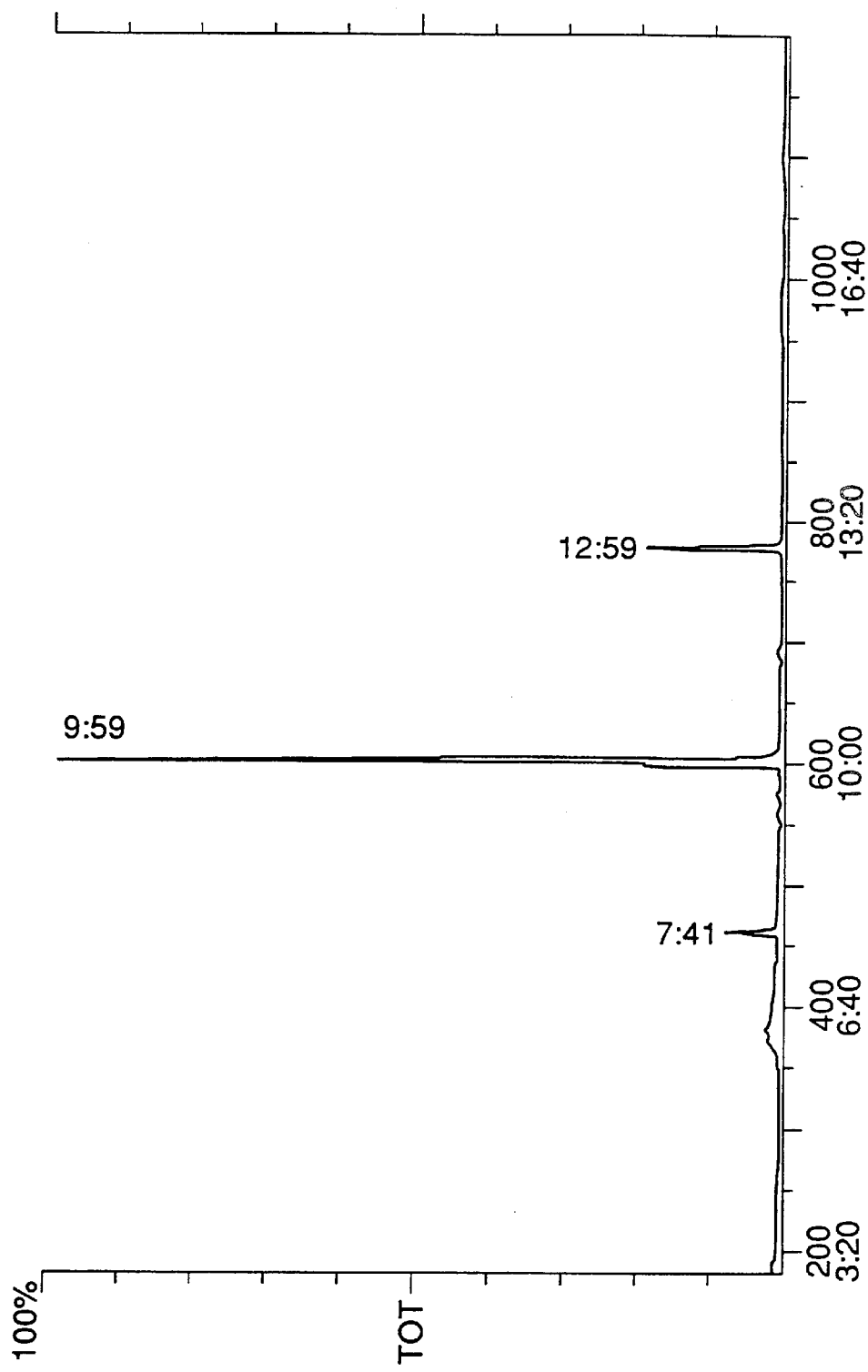
FIG. 3 shows a chromatogram of high-temperature desulfurization products of 4,6-dimethylbenzothiophene, which was obtained in gas chromatography and mass spectrometry.
Figure 4:
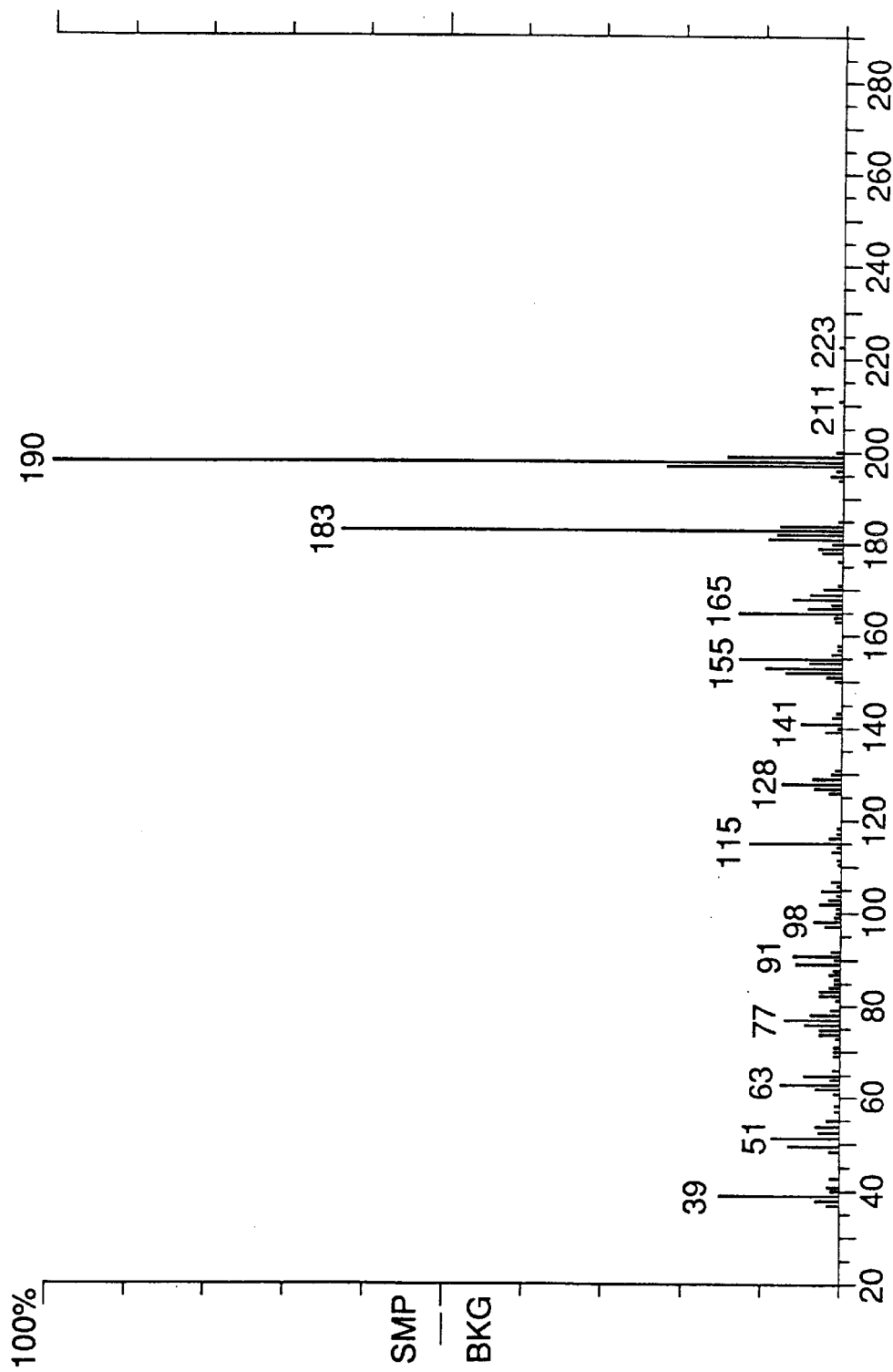
FIG. 4 shows a mass spectrum of a high-temperature desulfurization product of 4,6-dimethylbenzothiophene, which was obtained in gas chromatography and mass spectrometry.
Figure 5:
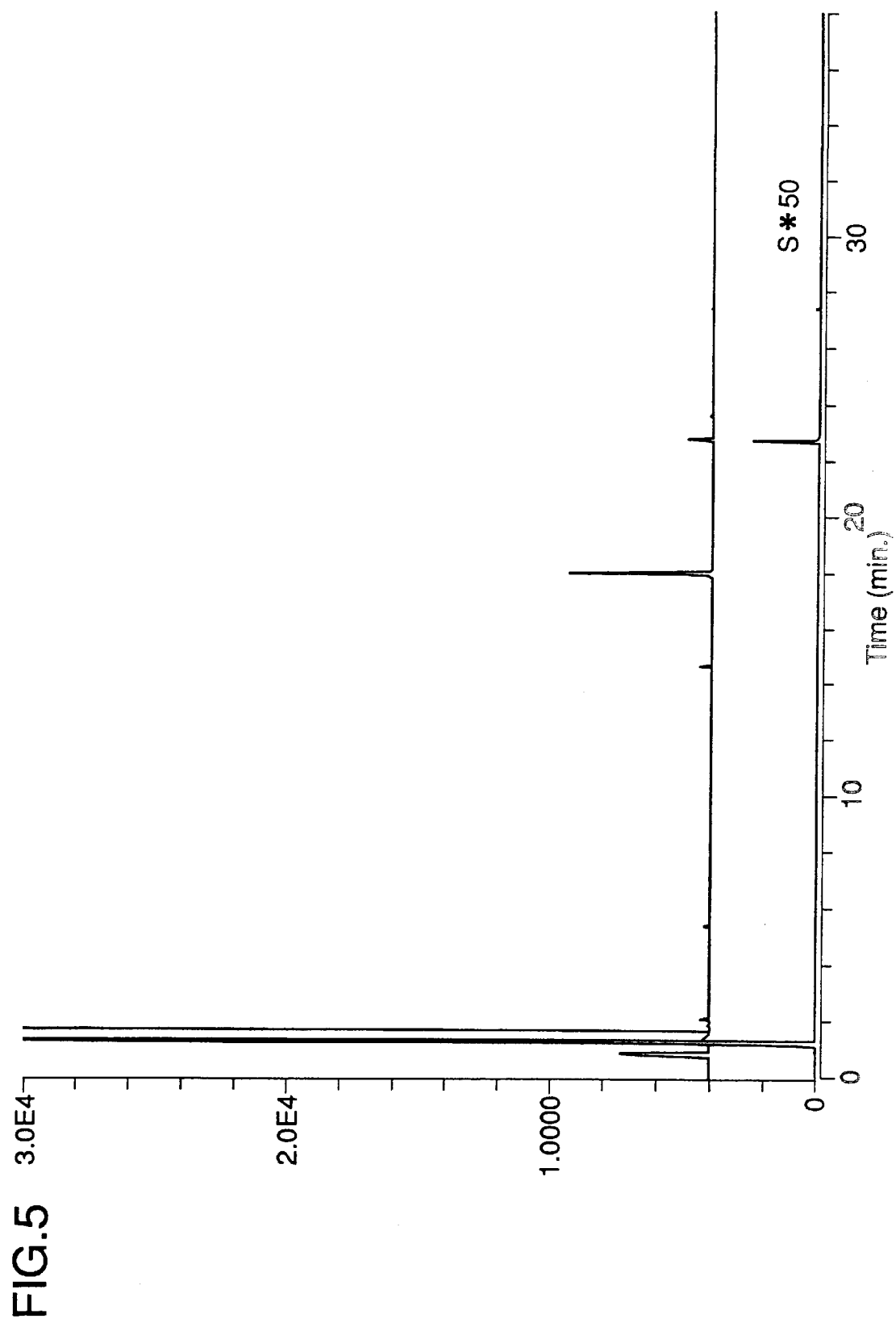
FIG. 5 shows a chromatogram of high-temperature desulfurization products of 4,6-dimethylbenzothiophene, which was obtained in gas chromatography/atomic emission analysis.

By way of one example, the method for degradation of 4,6-dimethyldibenzothiophene and the results are shown. Five milliliters high-temperature desulfurization medium containing 4,6-dimethyldibenzoth iophene (100 ppm) as a sole sulfur source was introduced into a test tube of 18 mm in diameter equipped with a stopper, and 0.1 ml of a suspension of Paenibacillus sp. A11-2 was added to it and cultured for 24 hours at 50° C. with shaking. When the turbidity of the culture at 660 nm reached 1.08, the culture was adjusted to pH 2.0 with 6 N hydrochloric acid and then extracted under stirring with ethyl acetate. The resulting extract was analyzed by gas chromatography, gas chromatography/mass spectrometry, and gas chromatography/atomic emission spectrometry. As shown in FIG. 2 (chromatogram obtained by gas chromatography), FIG. 3 (chromatogram obtained by gas chromatography/ mass spectrometry), FIG. 4 (mass spectrum obtained by gas chromatography/mass spectrometry), and FIG. 5 (chromatogram obtained by gas chromatography/atomic emission spectrometry), it was confirmed that 4,6-dimethyl dibenzothiophene was desulfurized and converted into a hydroxylated derivative.

Example 4
High-Temperature Degradation of Dibenzothiophene by Resting Cells

By way of one example, the resting cell reaction using the high-temperature desulfurizing microorganism Paenibacillus sp. A11-2 is described in detail.

Five milliliters of the high-temperature desulfurization medium described in Example 1 was introduced into a test tube with a stopper, and a colony on a storage plate (high-temperature desulfurization medium containing 1.5% agar) was inoculated into it via one platinum inoculation loop. The microorganism was cultured at 50° C. for 1 day with stirring, and the resulting culture was used as a stock of the microorganism. The microorganism for use in the resting cell reaction was prepared as follows: 100 ml high-temperature desulfurization medium containing 20 mg/l (20 ppm) dibenzothiophene was introduced into a 500 ml Erlenmeyer flask equipped with a baffle. Two milliliters of the above stock was inoculated into it and cultured at 50° C. with stirring at 160 r.p.m. until the $OD_{660}$ of the culture reached 0.5 (i.e., for about 15 hours). Then, the culture thus obtained was centrifuged at 8,000×g for 5 minutes to collect the bacterial cells. After removal of the supernatant, the bacterial cells were washed with 100 ml physiological saline and collected by centrifugation again under the same conditions. This washing procedure was repeated twice. The resulting bacterial cells were suspended again in 0.1 M phosphate buffer (pH 7.0) such that the $OD_{660}$ of the suspension reached about 20. This suspension was used as a microbial suspension for resting cell reaction.

The resting cell reaction was carried out in the following manner. Five hundred microliters of the above microbial suspension was introduced into a 7 ml test tube with a stopper and preheated at defined reaction temperature (37° C., 50° C. and 60° C.) for 15 minutes, and the temperature of the microbial suspension was adjusted to the same temperature as in the resting cell reaction. The ethanol solution (7.5 µl) of dibenzothiophene (10000 ppm) was added to the microbial suspension (final concentration of dibenzothiophene: 150 ppm) and subjected to the resting cell reaction by rotating inverted by it for 1 hour at 37° C., 50° C. and 60° C., respectively.

After the reaction, the microbial suspension was adjusted to about pH 2 with 6 N hydrochloric acid, and the dibenzothiophene and the resting cell reaction products were extracted with 0.3 ml ethyl acetate. The resulting extracts were analyzed by gas chromatography and gas chromatography/mass spectrometry, and it was thereby confirmed that 2-hydroxybiphenyl was formed as the degradation product of dibenzothiophene. The symbol "+" in Table 6 indicates that 2-hydroxybiphenyl was formed as the desulfurization product from the substrate dibenzothiophene. In this case, the substrate was not added to the reaction mixture until the reaction reached the predetermined reaction temperature by heating, so that one can exclude the possibility that the degradation of dibenzothiophene might have transiently proceeded during heating to the predetermined reaction temperature. By doing so, the result in Table 6 can reliably prove that the degradation of dibenzothiophene by the high-temperature desulfurizing microorganism occurs in the wide temperature range of 37 to 60° C. "−" indicates that 2-hydroxybephenyl was not detected and this can be seen in the results of the control where dibenzothiophene i.e. the substrate in the resting cell reaction system was not added.

TABLE 6

Resting Cell Reaction by High-Temperature Desulfurizing Microorganism

| Temperature | Degradation of Dibenzothiophene | Control (without dibenzothiophene) |
| --- | --- | --- |
| 37° C. | + | − |
| 50° C. | + | − |
| 60° C. | + | − |

Example 5. High-Temperature Degradation of Sulfur Compounds in Light Gas Oil

Degradation of organic sulfur compounds in light gas oil by the high-temperature desulfurizing microorganism was carried out in the same conditions as in Example 3. Ten milliliters of the medium and 2 ml of light gas oil containing 800 ppm sulfur were introduced into a 100 ml Erlenmeyer flask equipped with a stopper, and each of microbial precultures prepared as described in Example 1 was inoculated into it at a concentration of about 1% and cultured with stirring. The turbidity of each culture at 660 nm was determined in a spectrophotometer, and this turbidity was used to evaluate the degree of growth of the microorganism. The analysis of the total sulfur content was carried out by the same method and the same pyro-ultraviolet fluorescence method as in Example 3. As the control, the microorganism was grown simultaneously in the medium not containing any sulfur compound.

The results of the desulfurization of light gas oil by the high-temperature desulfurizing strains Paenibacillus sp. A11-1 and A11-2 are shown in Table 7.

TABLE 7

Desulfurization of Light Gas Oil by High-Temperature Desulfurization Microorganisms

| High-Temperature Desulfurization Microorganisms | Degree of Growth (OD660) | Degree of Desulfurization (%) |
| --- | --- | --- |
| Control | 0 | 0.0 |
| Paenibacillus sp. A11-1 | 1.08 | 7.0 |
| Paenibacillus sp. A11-2 | 1.20 | 11.0 |

As shown in Table 7, the growth of the desulfurizing microorganisms was accompanied by degradation of the organic sulfur compounds in light gas oil, and there occurred reduction in 7% and 11% of the sulfur content. In this example, it was revealed that light gas oil was desulfurized efficiently as the desulfurizing microorganism grew.

What is claimed is:

1. Paenibacillus sp. A11-1 having the ability to decompose organic sulfur compounds at high temperature.

2. Paenibacillus sp. A11-2 having the ability to decompose organic sulfur compounds at high temperature.

* * * * *

UNITED STATES PATENT AND TRADEMARK OFFICE
CERTIFICATE OF CORRECTION

PATENT NO. : 6,130,081
DATED : October 10, 2000
INVENTOR(S) : Jin Konishi; Yoshitaka Ishii; Kouichi Okumura; Masanori Suzuki It is certified that error appears in the above-identified patent and that said Letters Patent is hereby corrected as shown below:

<u>Title page,</u>
Item [62] Division of application no. 08/905,778, Jul. 29, 1997, Pat. No. 5,925,560.

Signed and Sealed this

Twenty-third Day of October, 2001

Attest:

*Nicholas P. Godici*

NICHOLAS P. GODICI
*Attesting Officer*   *Acting Director of the United States Patent and Trademark Office*